(12) United States Patent
Ahmady et al.

(10) Patent No.: US 12,644,037 B2
(45) Date of Patent: Jun. 2, 2026

(54) DETERMINING CLEAN-UP CHARACTERISTICS FOR DESIGNING WELLBORE FLUID

(71) Applicant: Halliburton Energy Services, Inc.,
Houston, TX (US)

(72) Inventors: Afshin Ahmady, Houston, TX (US);
Siva Rama Krishna Jandhyala, Katy,
TX (US); Ronnie Glen Morgan,
Waurika, OK (US)

(73) Assignee: Halliburton Energy Services, Inc.,
Houston, TX (US)

( * ) Notice: Subject to any disclaimer, the term of this
patent is extended or adjusted under 35
U.S.C. 154(b) by 281 days.

(21) Appl. No.: 18/494,051

(22) Filed: Oct. 25, 2023

(65) Prior Publication Data

US 2025/0137333 A1     May 1, 2025

(51) Int. Cl.
| | |
|---|---|
| *C09K 8/52* | (2006.01) |
| *E21B 37/00* | (2006.01) |
| *E21B 49/08* | (2006.01) |
| *G01N 33/24* | (2006.01) |
| *G01N 33/28* | (2006.01) |

(52) U.S. Cl.
CPC ............... *C09K 8/52* (2013.01); *E21B 37/00*
(2013.01); *E21B 49/08* (2013.01); *G01N*
*33/24* (2013.01); *G01N 33/2823* (2013.01)

(58) Field of Classification Search
CPC ...... G01N 33/24; G01N 33/2823; C09K 8/52;
E21B 37/00; E21B 21/003
See application file for complete search history.

(56) References Cited

U.S. PATENT DOCUMENTS

| | | | |
|---|---|---|---|
| 7,392,845 B2 * | 7/2008 | Berry ..................... | C09K 8/524 |
| | | | 507/261 |
| 7,906,464 B2 | 3/2011 | Davidson | |
| 8,371,381 B2 * | 2/2013 | Shindgikar ............. | E21B 33/13 |
| | | | 507/140 |
| 9,945,771 B2 | 4/2018 | Ahuja | |
| 10,563,113 B2 * | 2/2020 | AlDhufairi ............. | E21B 37/06 |
| 2022/0340803 A1 * | 10/2022 | Eyaa Allogo ............ | C09K 8/24 |

FOREIGN PATENT DOCUMENTS

| | | | | | |
|---|---|---|---|---|---|
| GB | 2481611 A | * | 1/2012 | ......... | G01N 33/2823 |
| WO | WO-2008144164 A1 | * | 11/2008 | ......... | G01N 33/2823 |

* cited by examiner

*Primary Examiner* — Jill E Culler
(74) *Attorney, Agent, or Firm* — Kilpatrick Townsend &
Stockton LLP

(57) ABSTRACT

A method can include positioning a filter cake sample
including a wellbore material in a filter cake insert of a
testing apparatus. The testing apparatus can include a slot,
walls, and a blade. The method can include applying increas-
ing amounts of force to the filter cake sample until a
threshold force is achieved. The threshold force can cause
the blade to displace the filter cake sample from the filter
cake insert. The method can include determining, based on
the threshold force, one or more clean-up characteristics
about the lost circulation material or the spacer material for
facilitating a decision regarding whether to use the wellbore
material for a well system.

19 Claims, 5 Drawing Sheets

400

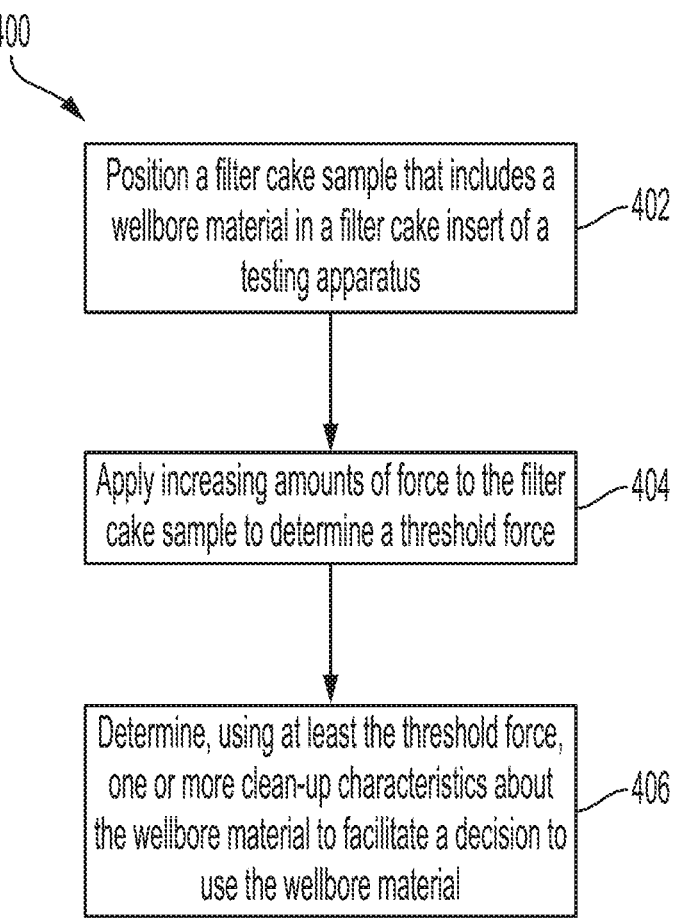

Position a filter cake sample that includes a wellbore material in a filter cake insert of a testing apparatus — 402

Apply increasing amounts of force to the filter cake sample to determine a threshold force — 404

Determine, using at least the threshold force, one or more clean-up characteristics about the wellbore material to facilitate a decision to use the wellbore material — 406

FIG. 4

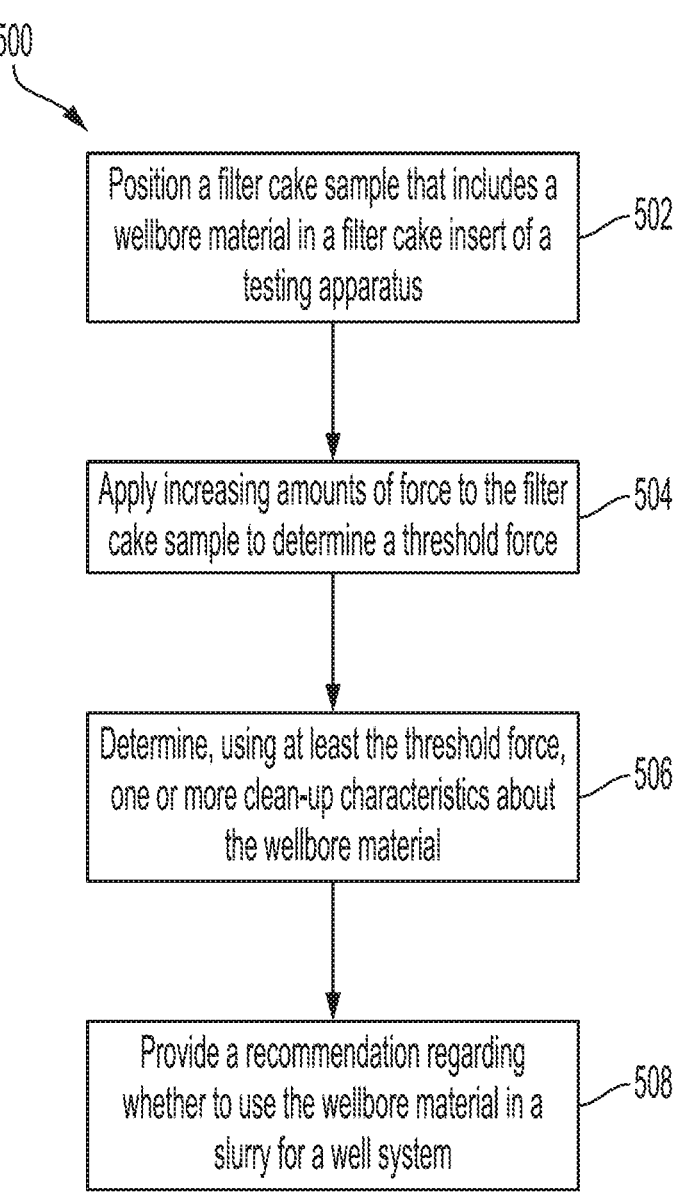

500

Position a filter cake sample that includes a wellbore material in a filter cake insert of a testing apparatus ⎯ 502

Apply increasing amounts of force to the filter cake sample to determine a threshold force ⎯ 504

Determine, using at least the threshold force, one or more clean-up characteristics about the wellbore material ⎯ 506

Provide a recommendation regarding whether to use the wellbore material in a slurry for a well system ⎯ 508

FIG. 5

DETERMINING CLEAN-UP CHARACTERISTICS FOR DESIGNING WELLBORE FLUID

TECHNICAL FIELD

The present disclosure relates generally to wellbore operations and, more particularly (although not necessarily exclusively), to determining clean-up characteristics of wellbore material to facilitate designing a fluid to be used in a wellbore.

BACKGROUND

Wellbore operations may include various equipment, components, methods, or techniques to form a wellbore, to complete a wellbore, to displace and release produced material, such as hydrocarbons, water, and the like, using a wellbore or flowline, and the like. In some examples, the wellbore operations may use one or more fluids such as cement, spacer fluid, including lost circulation material, and the like. The one or more fluids may be designed prior to being positioned in the wellbore, the flowline, or the like. One aspect of clean-up characteristics can include erosion resistance of the filter cake formed by the fluid adjacent to a wellbore well. Cleaning up a wellbore can involve removing mud filter cake, and a lost circulation material can stop or control fluid losses to in the wellbore. In this later case, the lost circulation material can plug cracks or pores that are causing losses, and may not be removed during wellbore cleaning process. It can be difficult to design or adjust the one or more fluids close to or during cementing jobs that can transport the lost circulation material (or package) to control or stop fluid losses to a reservoir.

BRIEF DESCRIPTION OF THE DRAWINGS

FIG. 4 is a flowchart of a process for determining clean-up characteristics of a slurry according to one example of the present disclosure.

FIG. 5 is a flowchart of a process for determining whether to use a slurry based on determined clean-up characteristics according to one example of the present disclosure.

DETAILED DESCRIPTION

Figure 1:
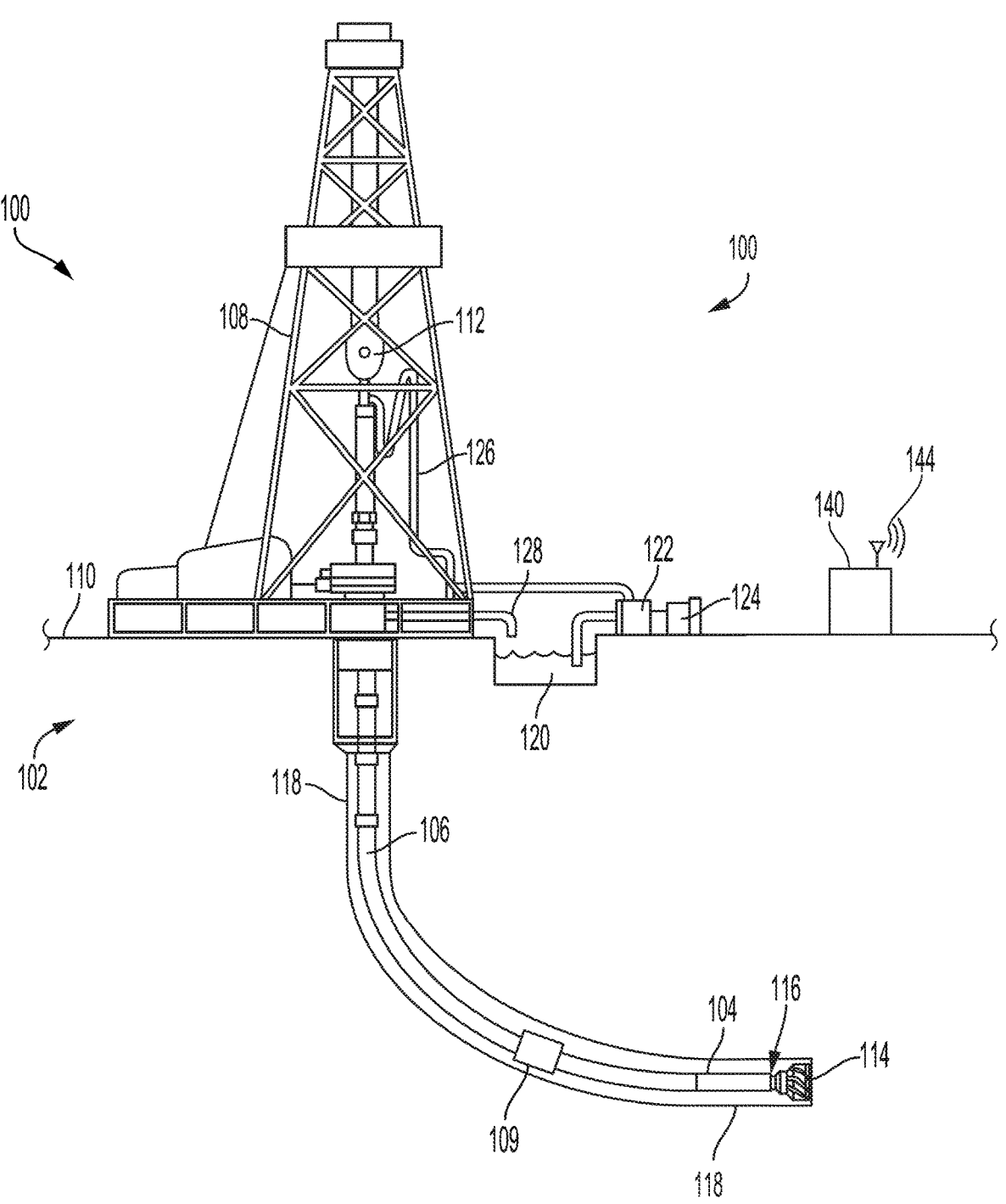
FIG. 1 is a diagram of a well system that can receive a slurry that has particular characteristics according to one example of the present disclosure.

Certain aspects and examples of the present disclosure relate to using a testing apparatus to determine clean-up characteristics about a wellbore material for designing a slurry. The slurry can be designed to be used in a well system that may include a wellbore or other conduit formed in a geological formation such as a subterranean formation, and sub-oceanic formation, and the like. The slurry can include a base fluid, such as water, brine, or the like, and the wellbore material, which may include a lost circulation material, a spacer material, a cement slurry, and the like. A lost circulation material may be used in the well system to prevent loss of fluid with respect to the well system, and a spacer material or cement slurry may be used in the well system to clean or otherwise remove unwanted material, such as mud, debris, and the like, from the well system. The testing apparatus can be used to determine the clean-up characteristics about the wellbore material. For example, a filter cake sample including the wellbore material can be placed in the testing apparatus and can be tested to determine the one or more clean-up characteristics. In some examples, the one or more clean-up characteristics can include a yield strength of the wellbore material, an expected erosion rate of the wellbore material in the well system, and the like.

Loss of circulation in a wellbore, in a geological formation, or otherwise with respect to a well system may occur (i) during or subsequent to a drilling operation, (ii) prior to, during, or subsequent to a cementing operation, and with respect to other stages of the well system. Lost circulation may involve losing material, such as wellbore fluid, cement, hydrocarbon material, and the like that may have been intended to be retained in the well system, to be produced from the well system, and the like. A lost circulation material can be added to drilling mud, to a spacer fluid, to cement, or to other slurries that can be positioned in the well system such as in the geological formation or in a wellbore of the well system. The lost circulation material may prevent or mitigate lost circulation, but the lost circulation material, if not effective, may at least eventually erode away from the well system either partially or completely, which may cause increases in lost circulation in the well system. For example, a lost circulation filter cake may be eroded in a permeable formation, which may allow lost circulation to resume in the permeable formation. Some characteristics, such as a clean-up rate, a resistance to erosion, or other suitable characteristics, about a lost circulation material may indicate a likelihood of success of the lost circulation material in the well system.

A comprehensive understanding of characteristics of a lost circulation filter cake can be used to improve lost circulation prevention in the well system. For example, the filter cake sample formed from the lost circulation material can be tested to determine a shear stress resistance, for example with respect to various fluids that may be encountered in the well system, of the lost circulation filter cake as well as other suitable clean-up characteristics of the lost circulation filter cake sample. Determining the clean-up characteristics of the lost circulation filter cake sample can facilitate selection of an optimized slurry for one or more wellbore operations performed with respect to the well system. For example, clean-up characteristics can be determined for a set of lost circulation materials included in the slurry of interest, and a particular lost circulation material with optimal clean-up characteristics can be determined to be included in a slurry to be positioned in the well system.

A testing apparatus can be used to determine clean-up characteristics and other suitable characteristics for lost circulation materials, spacer materials, and other suitable wellbore materials. In some examples, the testing apparatus may be similar to an adjusted version of a permeability plugging apparatus. A stable and representative filter cake sample can be generated for each lost circulation material, each spacer material, and the like. An undisturbed filter cake sample can be positioned in slot in a yield-strength-measurement setup, and a sliding blade can push the filter cake sample off of the slot at a particular applied force such as a threshold force. The particular force can be recorded and can be used to determine a shear stress resistance or the shear strength of the filter cake sample. Testing can be performed under one or more different pressures to consider an effect of differential pressure on the shear strength, or other clean-up characteristics, of the filter cake sample. A porosity of the filter cake sample can also be measured and used to determine yield stresses of the filter cake sample. In some examples, the foregoing information can be used to determine whether to use a particular wellbore material, to estimate an erosion rate of the particular wellbore material, or a combination thereof.

In some examples, the testing apparatus can include a slot, a set of walls, and a blade. The slot may be or include a base on which the set of walls and a filter cake sample can be positioned for testing. The blade can be positioned against the filter cake sample and can apply force to the filter cake sample to determine one or more clean-up characteristics about the filter cake sample. For example, increasing amounts of force can be applied from the blade to the filter cake sample until the filter cake sample is displaced from the slot via a threshold force. The clean-up characteristics may include a yield strength of the filter cake sample, a weight loss of the filter cake sample, a porosity of the filter cake sample, and the like. The testing apparatus can allow easy repeatability of testing for the filter cake sample.

In some examples, equipment for a permeability and plugging apparatus test setup can be customized or otherwise altered to form the testing apparatus. The testing apparatus can test the filter cake sample to determine a shear strength of the filter cake sample, a mud filter cake strength, and the like to indicate a likelihood of success of the filter cake sample in a well system. In some examples, the filter cake sample may be or include a solidified form of a slurry, which may be positioned in the well system, and that includes a base fluid, a lost circulation material or multiple lost circulation materials, a spacer material, or any combination thereof. Based on one or more tests involving the testing apparatus, well material, such as a lost circulation material, a spacer material, or the like, can be determined to be included, or to not be included, in a slurry to be positioned in the well system. For example, if the well material may easily be eroded in the well system, then the well material may be recommended to not be included in the slurry. Additionally or alternatively, if the well material may not easily be eroded in the well system, then the well material may be recommended to be included in the slurry. In other examples, a well material that is easily eroded in the well system may be recommended for including in the slurry.

In some examples, the testing apparatus can be used to determine input values that can be used to determine one or more characteristics about a filter cake sample. For example, the testing apparatus can be used to determine a threshold force, a contact area, and the like. The threshold force may be or include a force that, when exceeded, causes the filter cake sample to displace from the slot of the testing apparatus. Additionally or alternatively, the contact area can be or include an area of contact between the blade and the filter cake sample. Equation 1 can be used to determine a yield strength of the filter cake sample.

$$\tau = \frac{F_T}{A_C} \qquad \text{(Equation 1)}$$

In Equation 1, $\tau$ may be the yield strength of the filter cake sample, $F_T$ may be the threshold force, and $A_C$ may be the contact area between the filter cake sample and the walls surrounding it.

In some examples, the yield strength of the filter cake sample can be used to determine whether, or how much, erosion of the filter cake sample, or the well material included therein, may occur in a well system. The well system may experience shear stress on a wall of the well system or on other components of the well system. The shear stress can be estimated or otherwise determined and compared with the yield strength of the filter cake sample. In some examples, if the shear stress is larger than the yield strength, then the filter cake sample may erode, and if the shear stress is less than the yield strength, then the filter cake sample may not erode. Additionally or alternatively, a degree to which the filter cake sample may erode can be determined based on how much larger the shear stress is compared to the yield strength in examples in which the shear stress is larger than the yield strength.

These illustrative examples are given to introduce the reader to the general subject matter discussed herein and are not intended to limit the scope of the disclosed concepts. The following sections describe various additional features and examples with reference to the drawings in which like numerals indicate like elements, and directional descriptions are used to describe the illustrative aspects, but, like the illustrative aspects, should not be used to limit the present disclosure.

FIG. 1 a diagram of a well system 100 that can receive a slurry that has particular characteristics according to one example of the present disclosure. The well system 100 can include a wellbore 118 that can be used to extract hydrocarbons from a subterranean formation 102. The wellbore 118 can be drilled using the well system 100. The well system 100 may drive a bottom hole assembly (BHA) 104 positioned or otherwise arranged at the bottom of a drill-string 106 extended into the subterranean formation 102 from a derrick 108 arranged at the surface 110. The derrick 108 can include a kelly 112 used to lower and raise the drill-string 106. While the well system 100 is illustrated as being in a drilling stage, the well system 100 may additionally or alternatively be in other suitable stages of a well that may receive the slurry that has the particular characteristics.

The BHA 104 may include a drill bit 114 operatively coupled to a tool string 116, which may be moved axially within a drilled wellbore 118 and can be attached to the drill-string 106. The tool string 116 may include one or more wellbore tools 109 for determining conditions in the wellbore 118 or for performing other suitable wellbore operations. During operation, the drill bit 114 can penetrate the subterranean formation 102 to create the wellbore 118. The BHA 104 can control the drill bit 114 as the drill bit 114 advances into the subterranean formation 102. Fluid or "mud" from a mud tank 120 may be pumped downhole using a mud pump 122 that can be powered by an adjacent power source, such as a prime mover or motor 124. In some examples, the mud can be or include the slurry. The mud may be pumped from the mud tank 120, through a stand pipe 126, which can feed the mud into the drill-string 106 and can convey the mud to the drill bit 114. The mud can exit one or more nozzles (not shown) arranged in the drill bit 114 and can thereby cool the drill bit 114. After exiting the drill bit 114, the mud can circulate back to the surface 110 via the annulus defined between the wellbore 118 and the drill-string 106. Cuttings and mud mixture that can be passed through a flow line 128 can be processed such that a cleaned mud is returned down hole through the stand pipe 126.

In some examples, the drilling operation described above, one or more pre-cementing operations, a cementing operation, other completion operations, a stimulation operation, a production operation, or any other suitable well operations can be performed with respect to the wellbore 118. Some of the mud or other fluid, such as hydrocarbons, water, and the like, in the wellbore 118 may be lost, such as via lost circulation, to the subterranean formation 102. The fluid can be lost via perforations, which can be natural or artificial, which can be formed via drilling or stimulation, or the like, in the wellbore 118. The slurry can be used to reduce or eliminate the lost circulation. For example, the slurry may include a lost circulation material that may have been determined to be included in the slurry based on one or more clean-up characteristics of the lost circulation material. Additionally or alternatively, subsequent to a drilling operation being performed to form the wellbore 118, the wellbore 118 may be treated or otherwise prepared using the slurry. For example, the slurry can include a spacer material that can be used to clean the wellbore 118 to prepare for a cementing operation. The spacer material may have been determined to have one or more clean-up characteristics that may render the spacer material suitable for use in the well system 100.

The slurry can be designed, can be prepared, and can be positioned in the wellbore 118 for performing one or more wellbore operations. For example, the slurry can be designed with an optimized wellbore material, such as the lost circulation material or the spacer material, and the slurry can be prepared with the optimized wellbore material. The slurry can be positioned in the wellbore 118 for temporarily plugging or permanently plugging perforations in the wellbore 118 that may cause lost circulation. Additionally or alternatively, the slurry can be positioned in the wellbore 118 for cleaning, such as via abrasively removing mud, the wellbore 118. In some examples, the slurry may include a combination of the lost circulation material and the spacer material to facilitate a lost circulation operation and a cleaning operation with respect to the well system 100.

In some examples, the well system 100 can include a computing device 140 that can be positioned belowground, aboveground, onsite, in a vehicle, offsite, etc. As illustrated with respect to FIG. 1, the computing device 140 is positioned at the surface 110, but the computing device 140 can be positioned in any other suitable location. The computing device 140 can include a processor interfaced with other hardware via a bus. A memory, which can include any suitable tangible (and non-transitory) computer-readable medium, such as random-access memory ("RAM"), read-only memory ("ROM"), electrically erasable and programmable read-only memory ("EEPROM"), or the like, can embody program components that configure operation of the computing device 140. In some examples, the computing device 140 can include input/output interface components, such as a display, printer, keyboard, touch-sensitive surface, and mouse, and additional storage. The computing device 140 can be communicatively coupled to any suitable component of the well system 100 such as via a wireless connection or a wired connection.

The computing device 140 can include a communication device 144. The communication device 144 can represent one or more of any components that facilitate a network connection. In the example illustrated in FIG. 1, the communication device 144 is wireless and can include wireless interfaces such as IEEE 802.11, Bluetooth™, or radio interfaces for accessing cellular telephone networks (e.g., transceiver/antenna for accessing a CDMA, GSM, UMTS, or other mobile communications network). In some examples, the communication device 144 can use acoustic waves, surface waves, vibrations, optical waves, or induction, such as magnetic induction, for engaging in wireless communications. In other examples, the communication device 144 can be wired and can include interfaces such as Ethernet, USB, IEEE 1394, or a fiber optic interface. In an example with at least one other computing device, the computing device 140 can receive wired or wireless communications from the other computing device and perform one or more tasks based on the communications and with respect to the well system 100. For example, the computing device 140, or a non-transitory computer-readable medium included in the memory of the computing device 140, etc., can be used to determine an optimal wellbore material for including in the slurry for the well system 100.

Figure 2:
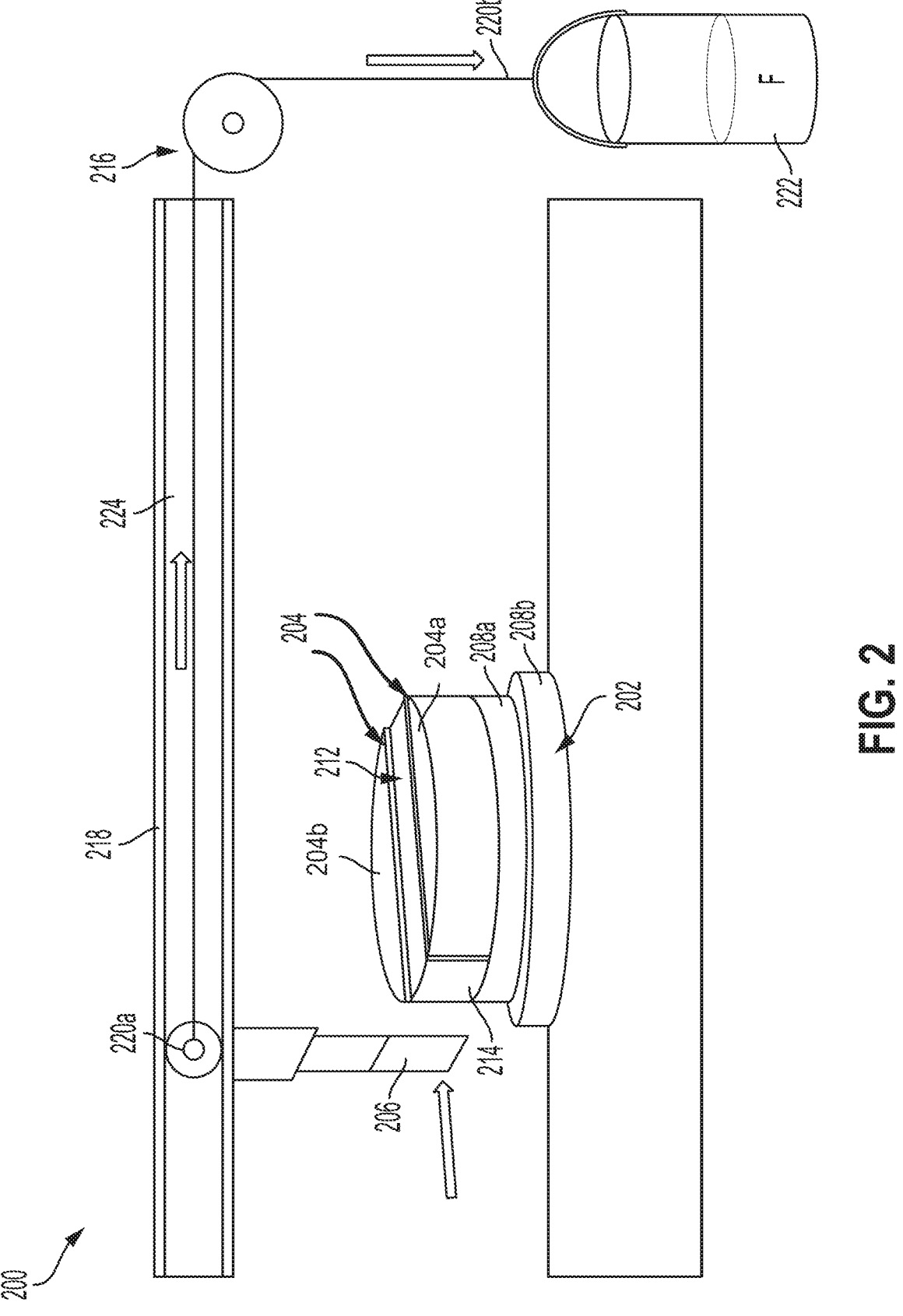
FIG. 2 is a diagram of a testing apparatus that can be used to determine clean-up characteristics for a slurry according to one example of the present disclosure.

FIG. 2 is a diagram of a testing apparatus 200 that can be used to determine clean-up characteristics for a slurry, or components thereof, according to one example of the present disclosure. As illustrated in FIG. 2, the testing apparatus 200 can include a slot 202, a set of walls 204, a blade 206, and other suitable components, devices, or the like. The slot 202, which may include a first base 208a and a second base 208b, can be sized to receive the set of walls 204. For example, each wall of the set of walls 204 can be positioned on the slot 202. The set of walls 204 may include two walls, such as a first wall 204a and a second wall 204b. In some examples, the first wall 204a of the set of walls 204 may have a first shape that may approximately be a partial circle, and the second wall 204b of the set of walls 204 may have a second shape that may additionally be approximately be a partial circle similar to the first wall 204a. Additionally or alternatively, each wall included in the set of walls 204 may be offset from one another to form a filter cake insert 212, which is a space that can be sized to receive a filter cake sample 214. The filter cake sample 214 may be or include a solidified form of a slurry that includes a wellbore material such as lost circulation material or spacer material.

The blade 206 may be positioned offset from the slot 202, the set of walls 204, or a combination thereof. For example, and as illustrated in FIG. 2, the blade 206 can be positioned vertically offset, such as above, the slot 202 and the set of walls 204. The blade 206 may be coupled, for example mechanically, with a pulley system 216 that may be positioned on a structural feature such as a beam 218. The beam 218 may be positioned vertically offset, such as above, the slot 202, the set of walls 204, the filter cake insert 212, the filter cake sample 214, or any combination thereof. The blade 206 may be positioned on a first end 220a of the pulley system 216, and a weight container 222 may be positioned on a second end 220b of the pulley system 216. The weight container 222 may be sized to receive increasing amounts of weight, for example in the form of fluid (e.g., water), discrete weight tiles or components, or the like. Additionally or alternatively, the blade 206 may be displaced across the beam 218 via a track 224 included in the beam 218. For example, adding weight to the weight container 222 may cause an equal force to be applied to the blade 206 to cause the blade 206 to displace along an axis of the track 224. In some examples, an alternative, such as a set of weight, a weight-applying device, or the like, to the weight container 222 may be used.

In some examples, the filter cake sample 214 can be positioned in the filter cake insert 212, and the blade 206 can be positioned abutting the filter cake sample 214. The filter cake sample 214 may be held in place in the filter cake insert 212 via cohesive forces within the filter cake sample 214, via adhesive forces between the filter cake sample 214 and the set of walls 204, the slot 202, or a combination thereof, and the like. In some examples, the adhesive forces between the filter cake sample 214 and the set of walls 204, the slot 202, or a combination thereof may mimic or otherwise represent forces between wellbore material included in the filter cake sample 214 and the well system 100. For example, the set of walls 204 may be or include metallic elements or compounds, polymeric material, or the like that may represent an adhesive surface of the well system 100. Representing the adhesive surface of the well system 100 can include the set of walls 204 having an adherence with respect to the filter cake sample 214 that is similar or identical to an expected adherence between the wellbore material included in the filter cake sample 214 and the wall of the well system 100. The blade 206 may be positioned to contact the filter cake sample 214, and increasing amounts of weight can be added to the weight container 222 to increase an amount of force applied from the blade 206 to the filter cake sample 214. A threshold force may be reached after a particular period of time, over which the increasing amounts of force may be applied to the blade 206 and the filter cake sample 214, and the threshold force may cause the filter cake sample 214 to displace out of the filter cake insert 212. The threshold force can be used to determine the one or more clean-up characteristics about the filter cake sample 214 or about a wellbore material included in the filter cake sample 214. For example, the threshold force can be used to determine a yield strength of the filter cake sample 214.

Figure 3:
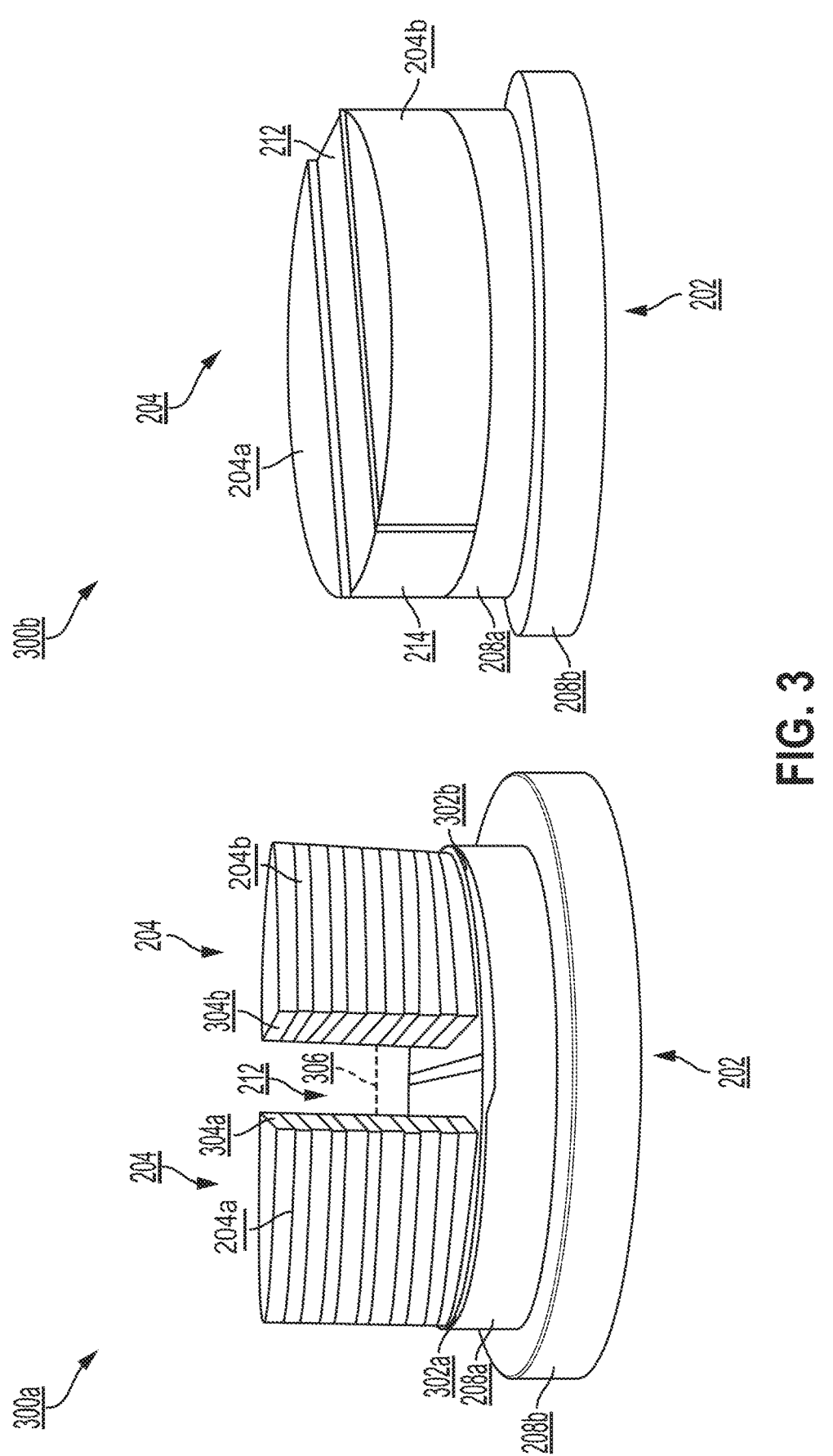
FIG. 3 is a diagram of a slot that can be used in a testing apparatus that can be used to determine clean-up characteristics for a slurry according to one example of the present disclosure.

FIG. 3 is a diagram of a slot that can be used in a testing apparatus that can be used to determine clean-up characteristics for a slurry according to one example of the present disclosure. FIG. 3 includes a first view 300a and a second view 300b. The first view 300a is a front view of a slot 202, of a testing apparatus 200, that includes a set of walls 204, and the second view 300b is a perspective view of the slot 202 having a filter cake sample 214 positioned in a filter cake insert 212. As illustrated in FIG. 3, for example via the first view 300a, the slot 202 may include a first base 208a and a second base 208b, though any other suitable number (e.g., one or more than two) of bases may be possible to be included in the slot 202. Additionally or alternatively, FIG. 3 illustrates the set of walls 204 as include a first wall 204a and a second wall 204b, though any other suitable number (e.g., one or more than two) of walls may be possible to be included in the set of walls 204.

In some examples, the set of walls 204 may be spaced apart from one another to form the filter cake insert 212. For example, the first wall 204a may be positioned at a first location 302a, and the second wall 204b may be positioned at a second location 302b. A first side 304a of the first wall 204a may be a distance 306 away from a second side 304b of the second wall 204b, and the first side 304a may be facing or opposing the second side 304b. In some examples, a width of the blade 206 may be approximately the same as the distance 306, an area of the blade 206 may be approximately the same as a surface area of the filter cake sample 214 when positioned in the filter cake insert 212, or the like. As illustrated in the second view 300b, the filter cake sample 214 can be sized to approximately fit into the filter cake insert 212, and the filter cake sample 214 can be positioned in the filter cake insert 212.

FIG. 4 is a flowchart of a process 400 for determining clean-up characteristics of a slurry, or a wellbore material included therein, according to one example of the present disclosure. At block 402, a filter cake sample, such as the filter cake sample 214, is positioned in a filter cake insert, such as the filter cake insert 212, of a testing apparatus such as the testing apparatus 200. The filter cake sample can be or include a solidified form of a slurry that can be used in a well system such as the well system 100. The slurry can include a base fluid, a lost circulation material, a spacer material, other suitable materials that can be included in the slurry, or any combination thereof. In some examples, the filter cake sample may be or include a representation of a lost circulation material deposit in the well system. Additionally or alternatively with respect to the lost circulation material, the filter cake sample can include a spacer material.

The testing apparatus can be used to conduct one or more tests on the filter cake sample. The testing apparatus can include a slot, a set of walls, a blade, and any other suitable device or component for the testing apparatus. The filter cake sample can be positioned in a filter cake insert, such as the filter cake insert 212, that can be formed by the set of walls of the testing apparatus. The blade can at least initially be positioned adjacent to the filter cake sample to contact the filter cake sample. The blade can be coupled with a first end of a pulley system, and a weight container or other weight-containing device can be coupled with a second end of the pulley system. The weight container may apply force, for example from gravity or other suitable sources, to the blade to cause the blade to displace or to apply approximately equal forces on the filter cake sample.

At block 404, increasing amounts of force are applied to the filter cake sample to determine a threshold force. The threshold force may be a force that, above which, cause the blade to displace the filter cake sample from the filter cake insert. In some examples, the increasing amounts of force may be applied incrementally, continuously, or the like. Incrementally increasing the force may involve adding a particular amount of weight at discrete time intervals. For example, five pounds (2.27 kg) may be added every one second, or any other examples of weight or mass and time. Additionally or alternatively, continuously increasing the force may involve continuing to increase weight at a constant rate without waiting for any particular time interval to elapse. The testing apparatus may record the threshold force, for example in response to detecting that the filter cake sample is displaced from the filter cake insert.

At block 406, one or more clean-up characteristics are determined for the filter cake sample or any component included therein. For example, the one or more clean-up characteristics may be determined for the filter cake sample, for a lost circulation material included in the filter cake sample, for a spacer material included in the filter cake sample, for other material included in the filter cake sample, or for any combination thereof. The one or more clean-up characteristics may be determined by using at least the threshold force. In some examples, the one or more clean-up characteristics may include a yield strength or a shear strength, an estimated rate of erosion, and the like. For example, the threshold force can be used, via Equation 1, to determine the yield strength. In another example, the threshold force can be used to determine the yield strength for determining the estimated rate of erosion or other suitable clean-up characteristics. Additionally or alternatively, the one or more clean-up characteristics can be used to facilitate a decision regarding whether to use the wellbore material in a slurry that can be used in a well system.

FIG. 5 is a flowchart of a process 500 for determining whether to use a slurry, or wellbore material included therein, based on determined clean-up characteristics according to one example of the present disclosure. At block 502, a filter cake sample, such as the filter cake sample 214, is positioned in a filter cake insert, such as the filter cake insert 212, of a testing apparatus such as the testing apparatus 200. The filter cake sample can be or include a solidified form of a slurry that can be used in a well system such as the well system 100. The slurry can include a base fluid, a lost circulation material, a spacer material, other suitable materials that can be included in the slurry, or any combination thereof. In some examples, the filter cake sample may be or include a representation of a lost circulation material deposit in the well system. Additionally or alternatively with respect to the lost circulation material, the filter cake sample can include a spacer material.

At block 504, increasing amounts of force are applied to the filter cake sample to determine a threshold force. The threshold force may be a force that, above which, cause the blade to displace the filter cake sample from the filter cake insert. In some examples, the increasing amounts of force may be applied incrementally, continuously, or the like. Incrementally increasing the force may involve adding a particular amount of weight at discrete time intervals. For example, five pounds (2.27 kg) may be added every one second, or any other examples of weight or mass and time. Additionally or alternatively, continuously increasing the force may involve continuing to increase weight at a constant rate without waiting for any particular time interval to elapse. The testing apparatus may record the threshold force, for example in response to detecting that the filter cake sample is displaced from the filter cake insert.

At block 506, one or more clean-up characteristics are determined for the filter cake sample or any component included therein. For example, the one or more clean-up characteristics may be determined for the filter cake sample, for a lost circulation material included in the filter cake sample, for a spacer material included in the filter cake sample, for other material included in the filter cake sample, or for any combination thereof. The one or more clean-up characteristics may be determined by using at least the threshold force. In some examples, the one or more clean-up characteristics may include a yield strength or a shear strength, an estimated rate of erosion, and the like. For example, the threshold force can be used, via Equation 1, to determine the yield strength. In another example, the threshold force can be used to determine the yield strength for determining the estimated rate of erosion or other suitable clean-up characteristics.

At block 508, a recommendation is generated and output regarding whether to use the wellbore material in a slurry for a well system. The recommendation may be generated based on the one or more clean-up characteristics. For example, the yield strength can be determined for the wellbore material, and the yield strength can be used to generate the recommendation. The recommendation may be or include an indication (i) to use the wellbore material in a slurry designed for the well system or (ii) to not use the wellbore material in a slurry designed for the well system. The recommendation may be the indication to use the wellbore material if the wellbore material is expected (e.g., based on the clean-up characteristics) to provide adequate (or better) performance in the well system. For example, if the wellbore material is expected to erode less than a threshold amount in the well system, then the recommendation may indicate to use the wellbore material in the slurry. In another example, if the wellbore material is expected to erode more than a threshold amount in the well system, then the recommendation may indicate to not use the wellbore material in the slurry.

In a particular example in which a lost circulation operation is scheduled to be performed in a wellbore, a particular lost circulation material can be selected for testing with respect to the wellbore. The particular lost circulation material can be positioned in the testing apparatus, for example via a filter cake sample, and the testing apparatus can be used to determine clean-up characteristics, including a yield strength, about the particular lost circulation material. The clean-up characteristics can be used to estimate a clean-up rate, or an expected erosion rate, of the particular lost circulation material in the wellbore. Additionally or alternatively, the clean-up characteristics, or the clean-up rate, can be used to determine an expected weight loss or an expected mass loss of the particular lost circulation material in the wellbore. The expected weight loss or the expected mass loss of the particular lost circulation material can be compared to a threshold value, such as a clearance in the wellbore, a perforation in the wellbore, or the like, and a recommendation regarding whether to use the particular lost circulation material can be generated. For example, if the weight loss or the expected mass loss of the particular lost circulation material exceeds the threshold value, then the recommendation may be generated to indicate to not use the particular lost circulation material in a slurry designed to be positioned in the wellbore. In another example, if the weight loss or the expected mass loss of the particular lost circulation material does not exceed the threshold value, then the recommendation may be generated to indicate to use the particular lost circulation material in the slurry designed to be positioned in the wellbore.

In another particular example in which a spacer operation or cleaning operation is scheduled to be performed in a wellbore, a particular spacer material can be selected for testing with respect to the wellbore. The particular spacer material can be positioned in the testing apparatus, for example via a filter cake sample, and the testing apparatus can be used to determine clean-up characteristics, including a yield strength, about the particular spacer material. The clean-up characteristics can be used to estimate a clean-up rate, or an expected erosion rate, of the particular spacer material in the wellbore. Additionally or alternatively, the clean-up characteristics, or the clean-up rate, can be used to determine an expected weight loss, an expected mass loss, or an expected cleaning capacity of the spacer material in the wellbore. The expected weight loss, the expected mass loss, or the expected cleaning capacity of the particular spacer material can be compared to a threshold value, such as a clearance in the wellbore, a perforation in the wellbore, a cleanliness of the wellbore, or the like, and a recommendation regarding whether to use the particular spacer material can be generated. For example, if the weight loss, the expected mass loss, or the expected cleaning capacity of the particular spacer material exceeds the threshold value, then the recommendation may be generated to indicate to use the particular spacer material in a slurry designed to be positioned in the wellbore. In another example, if the weight loss, the expected mass loss, or the expected cleaning capacity of the particular spacer material does not exceed the threshold value, then the recommendation may be generated to indicate to not use the particular spacer material in the slurry designed to be positioned in the wellbore.

In some aspects, methods and testing apparatuses for determining clean-up characteristics for designing a slurry are provided according to one or more of the following examples:

As used below, any reference to a series of examples is to be understood as a reference to each of those examples disjunctively (e.g., "Examples 1-4" is to be understood as "Examples 1, 2, 3, or 4").

Example 1 is a method for enabling selection of a wellbore fluid, the method comprising: receiving one or more clean-up characteristics about a wellbore material that includes a lost circulation material or a spacer material, the one or more clean-up characteristics indicating a resistance of a cake of the wellbore fluid to erosion in a well system; generating, using the one or more clean-up characteristics, a recommendation regarding whether to use the wellbore material in a slurry for the well system; and providing the recommendation regarding whether to use the wellbore material in the slurry for the well system to facilitate performing a wellbore operation with respect to the well system.

Example 2 is the method of example 1, wherein receiving the one or more clean-up characteristics comprises using a testing apparatus to determine the one or more clean-up characteristics, wherein the testing apparatus comprises: a slot sized to receive a set of walls and a filter cake sample; the set of walls positioned on the slot and spaced apart to define a filter cake insert; the filter cake sample positionable in the filter cake insert, the filter cake sample comprising a wellbore material that includes a lost circulation material or a spacer material; and a blade positionable to abut the filter cake sample while located in the filter cake insert, the blade having a first width that is approximately equal to a second width of the filter cake insert, wherein a threshold force is appliable from the blade to the filter cake sample to determine one or more clean-up characteristics about the wellbore material for facilitating a decision regarding whether to use the wellbore material in a slurry for a well system; and a longitudinal beam positioned vertically offset from the slot, wherein a pulley system is positioned on the longitudinal beam.

Example 3 is the method of any of examples 1-2, wherein receiving the one or more clean-up characteristics comprises determining a threshold force to determine the one or more clean-up characteristics, wherein the threshold force is identified by applying increasing amounts of force by adding incremental amounts of weight to a weight container coupled with the pulley system to cause the incremental amounts of weight to be applied from the pulley system to the blade and from the blade to a filter cake sample positioned in the slot.

Example 4 is the method of any of examples 1-3, wherein the filter cake sample is prepared by (i) mixing a slurry that comprises a base material and the wellbore material and (ii) solidifying the slurry to generate the filter cake sample.

Example 5 is the method of any of examples 1-3, further comprising determining a yield strength of the filter cake sample comprises dividing the threshold force by a contact area between the blade and the filter cake sample to determine the yield strength of the filter cake sample.

Example 6 is the method of example 1, wherein the one or more clean-up characteristics comprise a rate at which the cake of the wellbore material is expected to erode in the well system.

Example 7 is the method of example 1, wherein the one or more clean-up characteristics are determined by determining a yield strength of the cake of the wellbore material, and wherein the yield strength indicates a clean-up rate of the cake of the wellbore material in the well system.

Example 8 is a testing apparatus comprising: a slot sized to receive a set of walls and a filter cake sample; the set of walls positioned on the slot and spaced apart to define a filter cake insert; the filter cake sample positionable in the filter cake insert, the filter cake sample comprising a wellbore material that includes a lost circulation material or a spacer material; and a blade positionable to abut the filter cake sample while located in the filter cake insert, the blade having a first width that is approximately equal to a second width of the filter cake insert, wherein a threshold force is appliable from the blade to the filter cake sample to determine one or more clean-up characteristics about the wellbore material for facilitating a decision regarding whether to use the wellbore material in a slurry for a well system.

Example 9 is the testing apparatus of example 8, wherein the set of walls comprises two walls, wherein each wall of the two walls is shaped approximately as a partial circle, wherein a first wall of the two walls has a first flat side, wherein a second wall of the two walls has a second flat side, and wherein the two walls are arranged on the slot such that the first wall and the second wall are opposing one another and approximately parallel with respect to one another.

Example 10 is the testing apparatus of any of examples 8-9, wherein the filter cake insert is shaped approximately as a rectangular prism, wherein the first wall is a first side of the rectangular prism, and wherein the second wall is a second side of the rectangular prism opposite the first side.

Example 11 is the testing apparatus of example 8, further comprising: a longitudinal beam located vertically offset from the slot; and a pulley system located on the longitudinal beam, wherein the blade is coupled with a first end of the pulley system, and wherein a weight container is positioned on a second end of the pulley system opposite the first end.

Example 12 is the testing apparatus of any of examples 8 and 11, wherein increasing amounts of force are appliable to the blade by adding incremental amounts of weight to the weight container to cause the incremental amounts of weight to be applied from the pulley system to the blade and from the blade to the filter cake sample to determine the threshold force.

Example 13 is the testing apparatus of example 8, filter cake sample is generatable from a solidified form of a slurry that comprises a base material and the wellbore material.

Example 14 is the testing apparatus of example 8, wherein the one or more clean-up characteristics comprise a yield strength of the filter cake sample and a rate at which the wellbore material is expected to erode in the well system.

Example 15 is a method comprising: positioning a filter cake sample that comprises a wellbore material that includes a spacer material or a lost circulation material in a filter cake insert of a slot of a testing apparatus, the testing apparatus comprising: the slot; a set of walls positioned on the slot and spaced apart to define the filter cake insert; and a blade positioned abutting the filter cake insert, the blade having a first width that is approximately equal to a second width of the filter cake insert; applying increasing amounts of force to the filter cake sample until a threshold force is achieved, the threshold force causing the blade to displace the filter cake sample from the filter cake insert; and determining, based on the threshold force, one or more clean-up characteristics about the wellbore material for facilitating a decision regarding whether to use the wellbore material for a well system.

Example 16 is the method of example 15, wherein the testing apparatus further comprises a longitudinal beam positioned vertically offset from the slot, wherein a pulley system is positioned on the longitudinal beam, wherein the blade is coupled with a first end of the pulley system, and wherein a weight container is positioned on a second end of the pulley system opposite the first end.

Example 17 is the method of any of examples 15-16, wherein applying the increasing amounts of force comprises adding incremental amounts of weight to the weight container to cause the incremental amounts of weight to be applied from the pulley system to the blade and from the blade to the filter cake sample.

Example 18 is the method of example 15, wherein positioning the filter cake sample in the slot comprises preparing the filter cake sample by (i) mixing a slurry that comprises a base material and the wellbore material and (ii) solidifying the slurry to generate the filter cake sample.

Example 19 is the method of example 15, wherein the one or more clean-up characteristics comprise a rate at which the wellbore material is expected to erode in the well system.

Example 20 is the method of example 15, wherein determining the one or more clean-up characteristics comprises determining a yield strength of the filter cake sample, wherein the yield strength indicates a clean-up rate of the the wellbore material in the well system, and wherein determining the yield strength of the filter cake sample comprises dividing the threshold force by a contact area between the blade and the filter cake sample to determine the yield strength of the filter cake sample.

The foregoing description of certain examples, including illustrated examples, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure.

What is claimed is:

1. A method for enabling selection of a wellbore fluid, the method comprising:
receiving one or more clean-up characteristics about a wellbore material that includes a lost circulation material or a spacer material, the one or more clean-up characteristics indicating a resistance of a cake of the wellbore fluid to erosion in a well system, wherein receiving the one or more clean-up characteristics comprises using a testing apparatus to determine the one or more clean-up characteristics, and wherein the testing apparatus comprises:
a slot sized to receive a set of walls and a filter cake sample;
the set of walls positioned on the slot and spaced apart to define a filter cake insert;
the filter cake sample located in the filter cake insert, the filter cake sample comprising a wellbore material that includes a lost circulation material or a spacer material; and
a blade positionable to abut the filter cake sample while located in the filter cake insert, the blade having a first width that is approximately equal to a second width of the filter cake insert, wherein a threshold force is appliable from the blade to the filter cake sample to determine one or more clean-up characteristics about the wellbore material for facilitating a decision regarding whether to use the wellbore material in a slurry for a well system; and
a beam spaced apart from the slot, wherein a pulley system is positioned on the beam;
generating, using the one or more clean-up characteristics, a recommendation regarding whether to use the wellbore material in a slurry for the well system; and
providing the recommendation regarding whether to use the wellbore material in the slurry for the well system to facilitate performing a wellbore operation with respect to the well system.

2. The method of claim 1, wherein receiving the one or more clean-up characteristics comprises determining a threshold force to determine the one or more clean-up characteristics, wherein the threshold force is identified by adding incremental amounts of weight to a weight container coupled with the pulley system to cause the incremental amounts of weight to be applied from the pulley system to the blade and from the blade to a filter cake sample positioned in the slot.

3. The method of claim 2, wherein the filter cake sample is prepared by (i) mixing a slurry that comprises a base material and the wellbore material and (ii) solidifying the slurry to generate the filter cake sample.

4. The method of claim 2, further comprising determining a yield strength of the filter cake sample comprises dividing the threshold force by a contact area between the blade and the filter cake sample to determine the yield strength of the filter cake sample.

5. The method of claim 1, wherein the one or more clean-up characteristics comprise a rate at which the cake of the wellbore material is expected to erode in the well system.

6. The method of claim 1, wherein the one or more clean-up characteristics are determined by determining a yield strength of the cake of the wellbore material, and wherein the yield strength indicates a clean-up rate of the cake of the wellbore material in the well system.

7. A testing apparatus comprising:
a slot sized to receive a set of walls and a filter cake sample;
the set of walls positioned on the slot and spaced apart to define a filter cake insert;
the filter cake sample positionable in the filter cake insert, the filter cake sample comprising a wellbore material that includes a lost circulation material or a spacer material;
a blade positionable to abut the filter cake sample while located in the filter cake insert, the blade having a first width that is approximately equal to a second width of the filter cake insert, wherein a threshold force is appliable from the blade to the filter cake sample to determine one or more clean-up characteristics about the wellbore material for facilitating a decision regarding whether to use the wellbore material in a slurry for a well system;
a beam spaced apart from the slot; and
a pulley system located on the beam, the blade being configured to be coupled with a first end of the pulley system.

8. The testing apparatus of claim 7, wherein the set of walls comprises two walls, wherein each wall of the two walls is shaped approximately as a partial circle, wherein a first wall of the two walls has a first flat side, wherein a second wall of the two walls has a second flat side, and wherein the two walls are arranged on the slot such that the first wall and the second wall are opposing one another and approximately parallel with respect to one another.

9. The testing apparatus of claim 8, wherein the filter cake insert is shaped approximately as a rectangular prism, wherein the first wall is a first side of the rectangular prism, and wherein the second wall is a second side of the rectangular prism opposite the first side.

10. The testing apparatus of claim 7, wherein the beam is located vertically offset from the slot, and wherein a weight container is positioned on a second end of the pulley system opposite the first end.

11. The testing apparatus of claim 10, wherein increasing amounts of force are appliable to the blade by adding incremental amounts of weight to the weight container to cause the incremental amounts of weight to be applied from the pulley system to the blade and from the blade to the filter cake sample to determine the threshold force.

12. The testing apparatus of claim 7, filter cake sample is generatable from a solidified form of a slurry that comprises a base material and the wellbore material.

13. The testing apparatus of claim 7, wherein the one or more clean-up characteristics comprise a yield strength of the filter cake sample and a rate at which the wellbore material is expected to erode in the well system.

14. A method comprising:

positioning a filter cake sample that comprises a wellbore material that includes a spacer material or a lost circulation material in a filter cake insert of a slot of a testing apparatus, the testing apparatus comprising:

the slot;

a set of walls positioned on the slot and spaced apart to define the filter cake insert;

a blade positioned abutting the filter cake insert, the blade having a first width that is approximately equal to a second width of the filter cake insert; and a beam spaced apart from the slot, wherein a pulley system is positioned on the beam, and wherein the blade is coupled with a first end of the pulley system;

applying increasing amounts of force to the filter cake sample until a threshold force is achieved, the threshold force causing the blade to displace the filter cake sample from the filter cake insert; and determining, based on the threshold force, one or more clean-up characteristics about the wellbore material for facilitating a decision regarding whether to use the wellbore material for a well system.

15. The method of claim 14, wherein the testing apparatus further comprises a weight container positioned on a second end of the pulley system opposite the first end.

16. The method of claim 15, wherein applying the increasing amounts of force comprises adding incremental amounts of weight to the weight container to cause the incremental amounts of weight to be applied from the pulley system to the blade and from the blade to the filter cake sample.

17. The method of claim 14, wherein positioning the filter cake sample in the slot comprises preparing the filter cake sample by (i) mixing a slurry that comprises a base material and the wellbore material and (ii) solidifying the slurry to generate the filter cake sample.

18. The method of claim 14, wherein the one or more clean-up characteristics comprise a rate at which the wellbore material is expected to erode in the well system.

19. The method of claim 14, wherein determining the one or more clean-up characteristics comprises determining a yield strength of the filter cake sample, wherein the yield strength indicates a clean-up rate of the wellbore material in the well system, and wherein determining the yield strength of the filter cake sample comprises dividing the threshold force by a contact area between the blade and the filter cake sample to determine the yield strength of the filter cake sample.

* * * * *